US 6,666,822 B2

(12) United States Patent
Agano (10) Patent No.: US 6,666,822 B2
(45) Date of Patent: Dec. 23, 2003

(54) ULTRASONIC IMAGING METHOD AND APPARATUS (75) Inventor: Toshitaka Agano, Minami-Ashigara (JP)

(73) Assignee: Fuji Photo Film Co., Ltd., Kanagawa (JP)

( * ) Notice: Subject to any disclaimer, the term of this patent is extended or adjusted under 35 U.S.C. 154(b) by 0 days.

(21) Appl. No.: 10/114,118

(22) Filed: Apr. 3, 2002

(65) Prior Publication Data
US 2002/0147397 A1 Oct. 10, 2002

(30) Foreign Application Priority Data
Apr. 4, 2001 (JP) .......................... 2001-105700

(51) Int. Cl.⁷ ............................................... A61B 8/00
(52) U.S. Cl. ....................................... 600/437; 600/443
(58) Field of Search ................................. 600/437, 438, 600/440, 441–447, 450–455, 457–459; 367/7, 11, 130, 138, 150, 87, 140, 124; 342/81; 73/625, 626; 128/916

(56) References Cited

U.S. PATENT DOCUMENTS

| | | | | |
|---|---|---|---|---|
| 5,873,830 A | * | 2/1999 | Hossack et al. | 600/447 |
| 6,083,168 A | * | 7/2000 | Hossack et al. | 600/443 |
| 6,135,963 A | * | 10/2000 | Haider | 600/447 |
| 6,155,981 A | * | 12/2000 | Ermert et al. | 600/453 |
| 6,234,967 B1 | * | 5/2001 | Powers | 600/443 |
| 6,432,055 B1 | * | 8/2002 | Carp et al. | 600/437 |

* cited by examiner

Primary Examiner—Ali M. Imam
(74) Attorney, Agent, or Firm—Sughrue Mion, PLLC

(57) ABSTRACT

Ultrasonic imaging method and apparatus capable of displaying on a screen not only the shapes of internal organs but also the differences in properties thereof. The ultrasonic imaging method includes the steps of (a) obtaining plural kinds of image data by transmitting plural kinds of ultrasonic waves at different transmission power and receiving the plural kinds of ultrasonic waves reflected from an object to be inspected; and (b) performing arithmetic by using the plural kinds of image data obtained at step (a) to thereby figure out new image data.

18 Claims, 5 Drawing Sheets

ULTRASONIC IMAGING METHOD AND APPARATUS

BACKGROUND OF THE INVENTION

1. Field of the Invention

The present invention relates to an ultrasonic imaging method and an ultrasonic imaging apparatus for transmitting and receiving ultrasonic waves to obtain images for ultrasonic diagnosis and so on.

2. Description of a Related Art

Ultrasonic waves reflect at a site where the acoustic characteristic impedance varies, i.e., at an interface between different media. Ultrasonic images are constructed in the form of images on the basis of internal information on an object to be inspected such as a living body obtained by utilizing the above-mentioned nature of the ultrasonic waves. More specifically, the internal information of the object such as the living body is obtained by transmitting ultrasonic waves from a probe containing a plurality of ultrasonic transducers to the object and receiving the ultrasonic waves reflected from a reflector existing in the interior of the object. Such internal information is iteratively collected while changing the direction in which the ultrasonic waves are transmitted, which enables shapes and motions of the internal organs, etc., within the living body to be constructed as images. Therefore, such ultrasonic diagnosis may be an effective diagnostic method for diseases causing pathological change which can be recognized in terms of the shapes and motions of the internal organs, etc.

By the way, acoustic characteristics of various tissues in the living body are becoming apparent little by little. For example, tissues containing more collagen as intercellular substance have a higher ultrasonic velocity and a greater attenuation value, whereas tissues having a higher water content have a smaller attenuation constant. However, such specific correlation between the acoustic characteristics and various tissues within the living body has not yet fully been elucidated. For example, in tissues like pathologically changed tissues of myocardial infarction where intermingled denatured portions having an increased water content in place of melted protein, fiberized portions containing collagen as an ingredient created for restoring the denatured portions, and sound myocardial portions are intermingled, a multiplicity of strong echo sources may be present because the acoustic impedance is significantly different among the respective tissues. For this reason, the pathologically changed tissues are displayed with a higher brightness in the ultrasonic images. On the contrary, in the case of pathologically changed tissues, etc. where a part or a whole of an internal organ has uniformly varied, such strong echo sources are not present and hence the difference in properties of the tissues may not necessarily be judged by the ultrasonic images.

SUMMARY OF THE INVENTION

In view of the above point, an object of the present invention is to provide an ultrasonic imaging method and an ultrasonic imaging apparatus capable of displaying not merely the shapes of internal organs, etc., but also the difference in properties thereof in the ultrasonic diagnosis.

In order to solve the above problems, according to one aspect of the present invention, there is provided an ultrasonic imaging method comprising the steps of: (a) obtaining plural kinds of image data by transmitting plural kinds of ultrasonic waves at different transmission power and receiving the plural kinds of ultrasonic waves reflected from an object to be inspected; and (b) performing arithmetic by using the plural kinds of image data obtained at step (a) to thereby figure out new image data.

According to one aspect of the present invention, there is provided an ultrasonic imaging apparatus comprising: ultrasonic wave transmission/reception means having a plurality of ultrasonic transducers, for transmitting ultrasonic waves toward an object to be inspected and receiving the ultrasonic waves reflected from the object to output a detection signal; signal processing means for generating image data on the basis of the detection signal output from the ultrasonic wave transmission/reception means; control means for controlling the ultrasonic wave transmission/reception means to vary transmission power of the ultrasonic waves to be transmitted so as to transmit and receive plural kinds of ultrasonic waves at different transmission power; storage means for accumulating image data output from the signal processing means to thereby store plural kinds of image data obtained by transmitting and receiving plural kinds of ultrasonic waves at different transmission power; and arithmetic means for performing arithmetic by using the plural kinds of image data stored in the storage means to thereby figure out new image data.

According to the present invention, plural kinds of ultrasonic images obtained by transmitting and receiving plural kinds of ultrasonic waves at different transmission power are combined, so that tissues different in properties within the interior of the object can be extracted and displayed.

BRIEF DESCRIPTION OF THE DRAWINGS

The above and other objects, aspects, features and advantages of the present invention will become more apparent from the following detailed description when taken in conjunction with the accompanying drawings, in which.

DESCRIPTION OF THE PREFERRED EMBODIMENTS

Preferred embodiments of the present invention will now be described with reference to the drawings. The same components are designated by the same reference numeral and an explanation thereof will be omitted.

Figure 1:
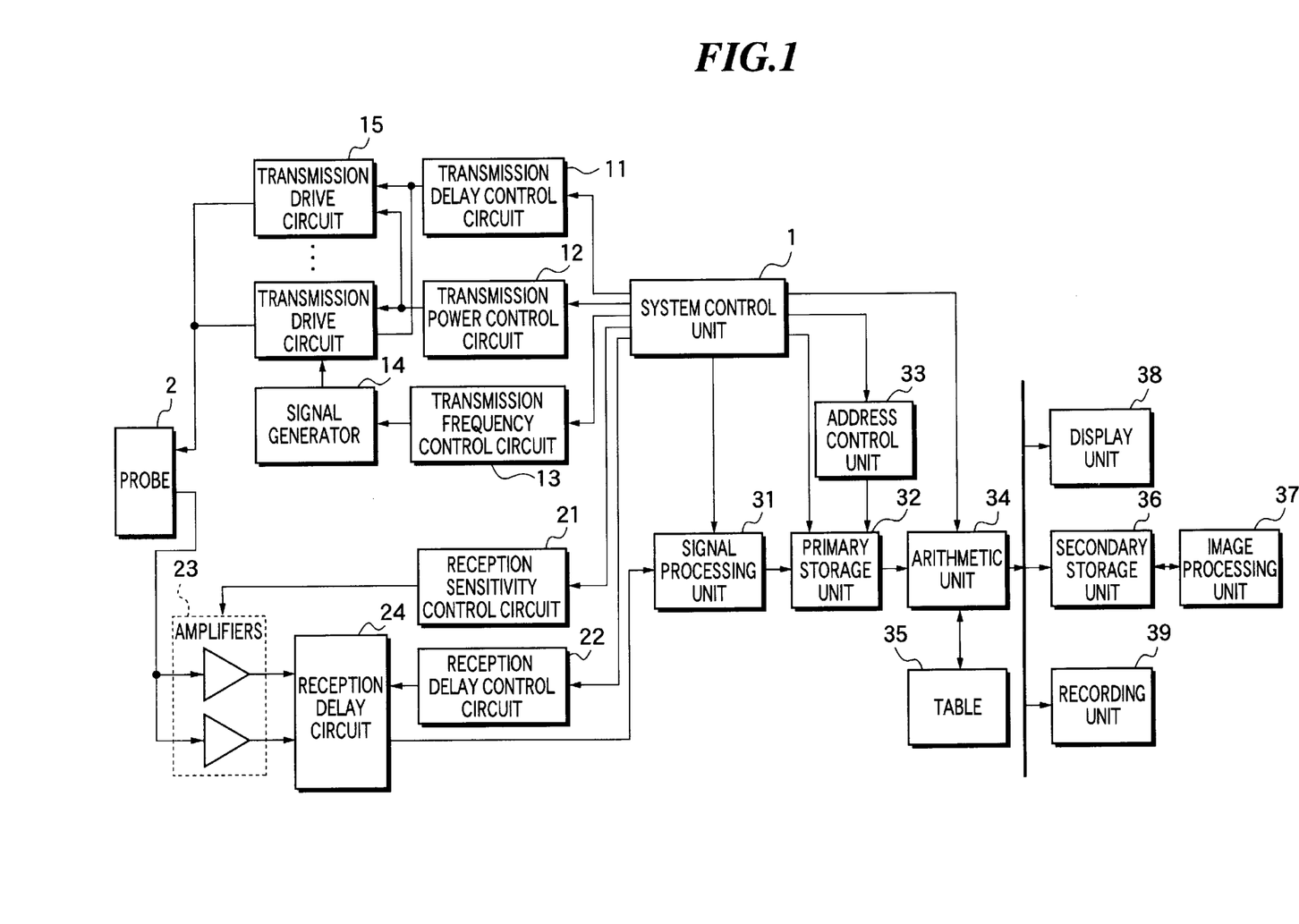
FIG. 1 is a block diagram showing the configuration of an ultrasonic imaging apparatus according to an embodiment of the present invention.

FIG. 1 is a block diagram showing an ultrasonic imaging apparatus according to an embodiment of the present invention.

Referring to FIG. 1, a system control unit 1 controls the entire system to acquire combined images by arithmetically processing plural kinds of frame data which are obtained based on signals acquired by transmitting plural kinds of ultrasonic waves at different transmission power and receiving the ultrasonic waves reflected from a reflector.

Figure 2:
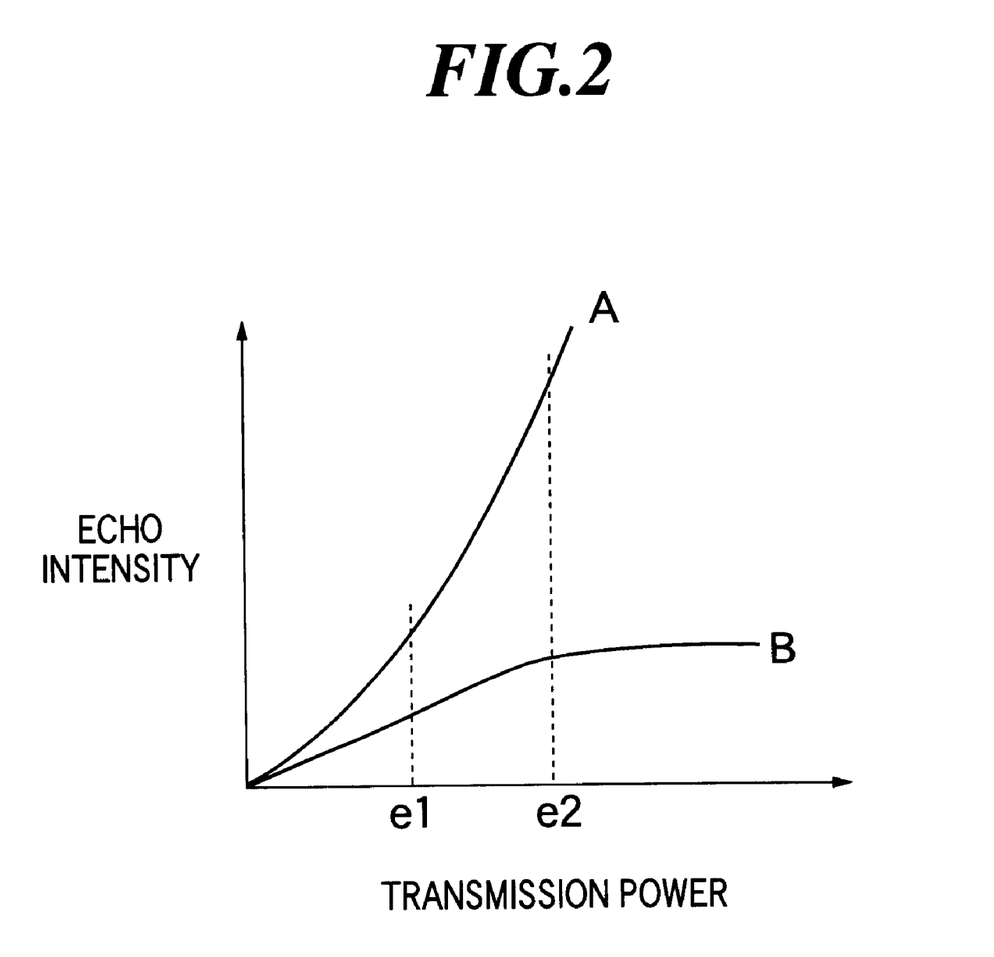
FIG. 2 illustrates an example of echo intensity characteristics of the internal tissues with respect to transmission power.

The reason will be explained why the ultrasonic imaging apparatus makes use of the plural kinds of ultrasonic waves transmitted at different transmission power. FIG. 2 shows echo intensity vs. transmission power as to reflectors A and B which exist within the interior of a living body as an object to be inspected. As can be seen in FIG. 2, such acoustic characteristics can vary diversely depending on the reflectors such as internal organs, e.g., including ones like reflector A having an acoustic characteristic indicative of a response in the form of an exponential function and ones like reflector B indicating a linear response to transmission power within a specified range but showing no change out of the specified. Thus, it is possible to extract an image of a specific internal organ, etc. by multiplying by appropriate coefficients a plurality of ultrasonic images, which are obtained by transmitting and receiving ultrasonic waves at at least two different kinds of transmission power, and finding the difference therebetween, thereby canceling the background indicative of linear acoustic characteristics with respect to the ultrasonic transmission power.

A probe 2 includes an ultrasonic transducer array having a plurality of ultrasonic transducers which are arranged one-dimensionally or two-dimensionally. As the ultrasonic transducers, vibrators can be used which are made of piezoelectric ceramics represented by PZT(Pb (lead) zirconate titanate) or polymer piezoelectric elements such as PVDF (polyvinyl difluoride). The vibrators have electrodes attached thereto and are connected via lead wires to an electronic circuit included in a main body of the ultrasonic imaging apparatus. The probe 2 may include a backing material for supporting the vibrators and providing acoustic attenuation to the vibrators, an acoustic matching layer ensuring effective transmission of ultrasonic waves, and an acoustic lens for gathering the ultrasonic waves.

The ultrasonic imaging apparatus further includes a transmission delay control circuit 11 for controlling ultrasonic wave transmitting/receiving conditions under the control of the system control unit 1, a transmission power control circuit 12, a transmission frequency control circuit 13, a reception sensitivity control circuit 21 and a reception delay control circuit 22.

In conformity with the control of the system control unit 1, the transmission frequency control circuit 13 controls a signal generator 14 in order to transmit ultrasonic waves having a predetermined frequency. The signal generator 14 generates signals in accordance with the control of the transmission frequency control circuit 13. A plurality of transmission drive circuits 15 amplify and delay the signals generated by the signal generator 14, to thereby output drive signals. On the basis of the drive signals, the probe 2 transmits ultrasonic waves to an object to be inspected and receives the ultrasonic waves reflected from the object to output detection signals. The detection signals are amplified by a plurality of amplifiers 23.

The transmission power control circuit 12 controls the amplitude of the drive signals output from the plurality of transmission drive circuits 15 so that the ultrasonic wave transmission power is controlled. The transmission delay control circuit 11 controls the delay time of the drive signals output from the plurality of transmission drive circuits 15. This allows each of the plurality of ultrasonic transducers included in the probe 2 to transmit ultrasonic waves having a phase difference corresponding to the time difference of the drive signals, at predetermined transmission power, toward the object to be inspected. Ultrasonic beams are thus formed by wavefront combining of such plurality of ultrasonic waves.

The reception sensitivity control circuit 21 controls gains of the plurality of amplifiers 23 to thereby control the reception sensitivity. The reception delay control circuit 22 controls the delay time of the detection signals in the reception delay circuit 24. A signal processing unit 31 subjects output signals of the reception delay circuit 24 to log compression, detection, analog-to-digital conversion and other processing, to create image data for output.

Under the control of the system control unit 1, an address control unit 33 provides as its output an address for controlling the storage region for the output image data. In accordance with the address, a primary storage unit 32 sequentially stores the image data output from the signal processing unit 31. Those image data are stored in separate regions corresponding to ultrasonic wave transmission power to constitute frame data for each transmission power. In this manner, the primary storage unit 32 stores frame data obtained as a result of transmission/reception of ultrasonic waves in accordance with different transmission power.

A table 35 stores coefficients for use in combining a plurality of frame data stored in the primary storage unit 32. Referring to the table 35, an arithmetic unit 34 executes arithmetic processing on the frame data stored in the primary storage unit 32 to create combined image data. The created combined image data are stored in a secondary storage unit 36 and displayed on a screen of a display unit 38 such as a CRT. An image processing unit 37 subjects the combined image data to interpolation, response modulation processing, gradation processing or other processing. A recording unit 39 records the combined image data on a recording medium such as a hard disk or a magneto optical disk (MO).

The ultrasonic imaging apparatus according to this embodiment may be of an independent type which incorporates the secondary storage unit 36, the display unit 38 and the recording unit 39 into the main body, or may be of a network connection type which is connected via a network to the secondary storage unit 36, the display unit 38, the recording unit 39 and so on.

Figure 3:
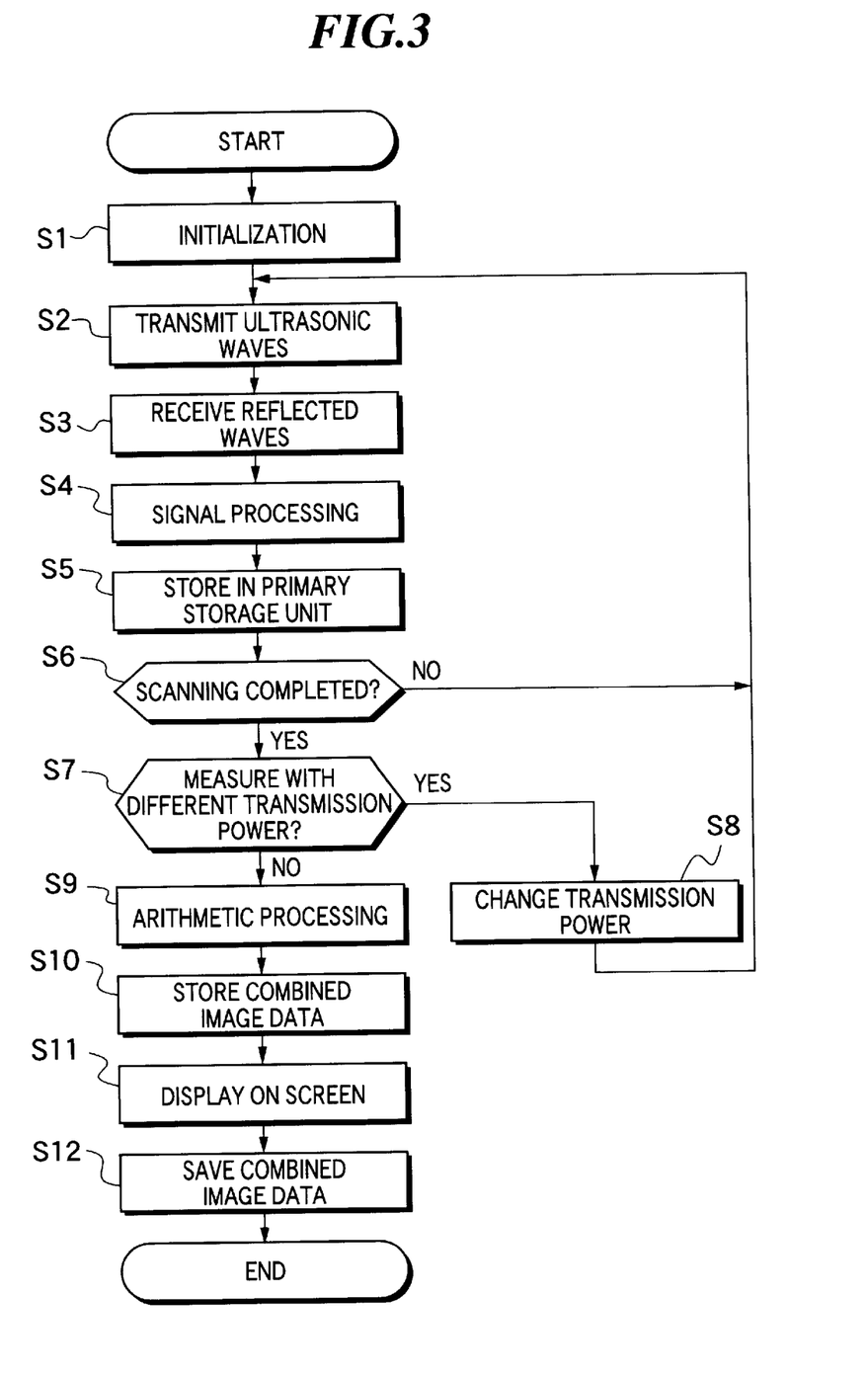
FIG. 3 is a flowchart showing the operations of the ultrasonic imaging apparatus according to the embodiment of the present invention.

Operations of the ultrasonic imaging apparatus according to this embodiment will then be described with reference to FIGS. 1–3. FIG. 3 is a flowchart showing the operations of the ultrasonic imaging apparatus according to this embodiment.

Initialization is first performed at step S1. More specifically, ultrasonic wave transmission power $e_1$ and ultrasonic wave transmission power $e_2$ are set in order to transmit plural kinds of ultrasonic waves at different transmission power. Herein, a frequency of the ultrasonic waves to be transmitted may be set. After the initialization, the system control unit 1 first sends control signals to the transmission power control unit 12 and the transmission frequency control unit 13 in order to transmit ultrasonic waves at the transmission power $e_1$, and sends address control signals to the address control unit 33 in order to control the image data storage region.

Then at step S2, ultrasonic waves at the transmission power $e_1$ are transmitted from the probe 2 toward the object to be inspected. That is, under the control of the transmission frequency control circuit 13, the signal generator 14 generates signals having a predetermined frequency and supplies the signals to the transmission drive circuits 15. The transmission drive circuits 15 impart a given delay to the signals under the control of the transmission delay control circuit 11, and send drive signals to the probe 2 at the transmission power $e_1$ controlled by the transmission power control circuit 12. This allows the ultrasonic transducers included in the probe 2 to vibrate and transmit ultrasonic waves to the object.

The transmitted ultrasonic waves are reflected from the reflector existing in the interior of the object, and at step S3 the reflected waves are received and converted into electric signals by the ultrasonic transducers, which electric signals are output as detection signals.

The detection signals are subjected to various signal processing. More specifically, the detection signals are amplified by the amplifiers 23 and entered into the reception delay circuit 24 to have a given delay under the control of the reception delay control circuit 22. The output signals from the reception delay circuit 24 are subjected in the signal processing unit 31 to log compression, detection, analog-to-digital conversion and other processing, and then output as image data. The output image data are stored in the primary storage unit 32 at step S5.

Such transmission/reception of the ultrasonic waves at steps S2 to S5 is iterated a plurality of times to effect the ultrasonic beam scanning (step S6), whereby image data are stored in the primary storage unit 32 so that frame data reflecting the acoustic characteristics as to the transmission power $e_1$ are obtained. It is to be understood that the ultrasonic wave transmission timing at step S2 may be set such that the next ultrasonic wave is transmitted without waiting for the completion of the signal processing and the completion of image data storage at step S4 and S5, as long as it can be separated from the precedingly transmitted ultrasonic wave.

It is then judged at step S7 whether or not the measurement is to be continued by changing the ultrasonic wave transmission power. If affirmative, then the procedure goes to step S8 in which the system control circuit 1 changes and issues various control signals in order to transmit ultrasonic waves at the transmission power $e_2$. In response to this, the transmission power control circuit 12 and the transmission frequency control circuit 13 control the transmission drive circuits 15 and the signal generator 14 respectively for the purpose of transmitting ultrasonic waves at the transmission power $e_2$ set at step S1. The address control unit 33 enters into the primary storage unit 32 an address for designating a storage region which stores image data obtained by transmitting and receiving the ultrasonic waves at the transmission power $e_2$.

Furthermore, steps S2 to S6 are iterated so that the image data obtained by transmitting and receiving the ultrasonic waves at the transmission power $e_2$ are accumulated in the primary storage unit 32 to constitute frame data.

Then, the system control unit 1 changes and issues various control signals in order to again transmitting ultrasonic waves at the transmission power $e_1$.

Thus, by alternately iterating the transmission of the ultrasonic waves at the transmission power $e_1$ and the transmission of the ultrasonic waves at the transmission power $e_2$, the frame data obtained by transmitting and receiving the ultrasonic waves at the transmission power $e_1$ and the frame data obtained by transmitting and receiving the ultrasonic waves at the transmission power $e_2$ are alternately stored in the primary storage unit 32.

Then, at step 9, the arithmetic unit 34 performs arithmetic processing for the frame data stored in the primary storage unit 32, while referring to the table 35.

Description will be made herein of the arithmetic processing in case of transmitting and receiving two different ultrasonic waves at different transmission power. In this case, a reflector A in FIG. 2 is a contrast medium A flowing in a blood vessel, while a reflector B is an internal organ B.

Figure 4A:
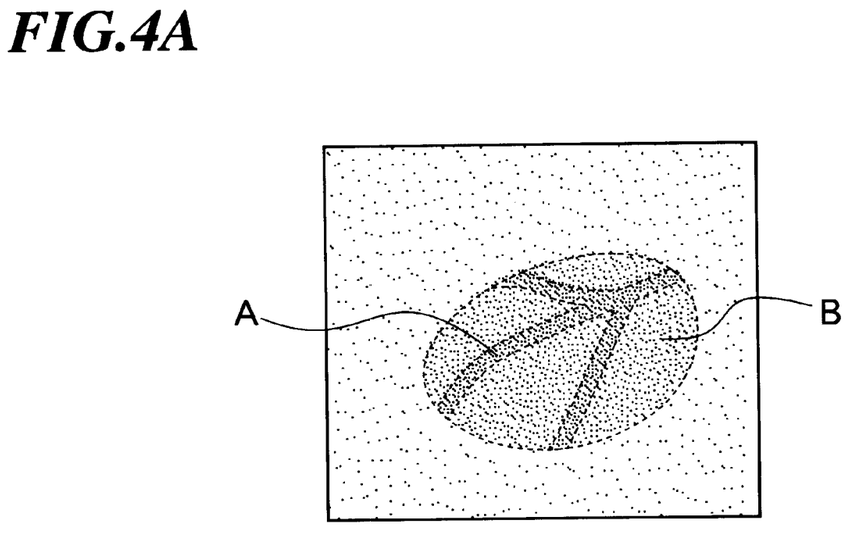
FIG. 4a is a diagram showing an image obtained by transmission/reception of ultrasonic waves at transmission power $e_1$.
Figure 4B:
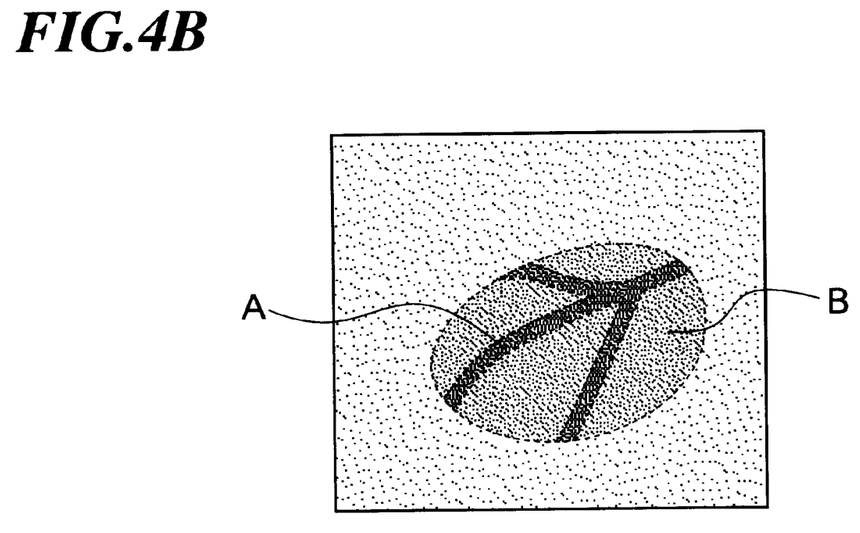
FIG. 4b is a diagrams showing an image obtained by transmission/reception of ultrasonic waves at transmission power $e_2$.

FIG. 4a illustrates an image made up on the basis of frame data $D(e_1)$ acquired by transmission/reception of ultrasonic waves at the transmission power $e_1$, whilst FIG. 4b illustrates an image made up on the basis of frame data $D(e_2)$ acquired by transmission/reception of ultrasonic waves at the transmission power $e_2$. In FIGS. 4a and 4b, broken lines denote a boundary between an image of the contrast medium A and an image of the internal organ B, and also denote a boundary between the internal organ B and the background.

As seen in FIGS. 4a and 4b, when the transmission power rises from $e_1$ to $e_2$, the brightness of the entire screen including the background increases accordingly. However, in case of the reflectors having nonlinear acoustic characteristics with respect to the ultrasonic wave transmission power, like the contrast medium A and the internal organ B, an increase of the transmission power will not uniformly result in an increase of the echo intensity. For example, the increased transmission power leads to a sharply increased echo intensity as in the contrast medium A, but to insignificant change as in the internal organ B. It is therefore possible to extract image data of the contrast medium A and of the internal organ B by multiplying the frame data $D(e_1)$ and $D(e_1)$ by appropriate coefficients so as to cancel the background and finding the difference therebetween.

Let $G(e_1, e_2)$ be combined image data which have been arithmetically processed, and $k_1$ and $k_2$ be positive coefficients stored in the table 35, then the combined image data can be figured out from $$G(e_1, e_2) = k_2 \times D(e_2) - k_1 \times D(e_1)$$

The frame data $D(e_1)$ and $D(e_2)$ used herein are preferably shortest interframe data.

As a result of such arithmetic processing, as is clear from reference to FIG. 2, the data on the contrast medium A are positive values and data on the internal organ B are negative values.

In order to use these data for image display, a certain value may be added to the combined image data. More specifically, let C be a constant, then the combined image data $G'(e_1, e_2)$ for display can be given as $$G'(e_1, e_2) = G(e_1, e_2) + C$$

Figure 5:
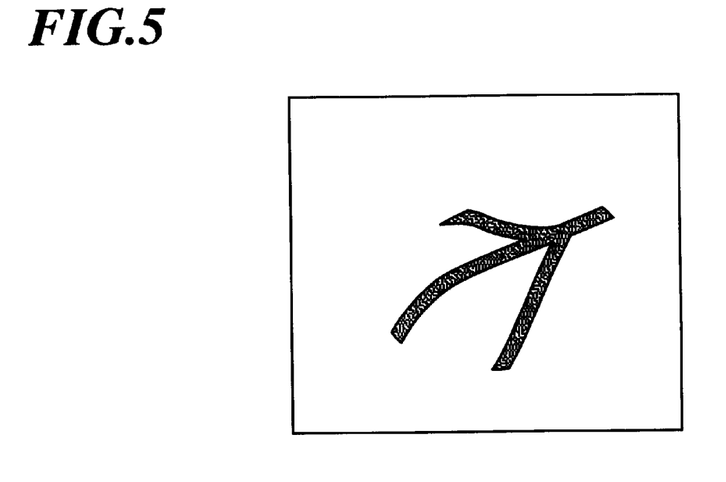
FIG. 5 illustrates an image constructed on the basis of combined image data which have been arithmetically processed.

FIG. 5 shows an image defined by the thus obtained combined image data $G'(e_1, e_2)$.

The arithmetically processed combined image data are stored in the secondary storage unit 36 at step S10. The combined image data may be subjected to image processing such as interpolation, response modulation processing and gradation processing by the image processing unit 37.

Furthermore, on the basis of such combined image data, combined images may be displayed on the screen of the display unit 38 such as a CRT (step S11) or saved on various record media in the recording unit 39 (step S12).

When displaying a combined image, display of only the tissue extracted may possibly make the whole image unclear. In such an event, additional processing such as coloring on each extracted tissue may be effected for display.

Figure 6:
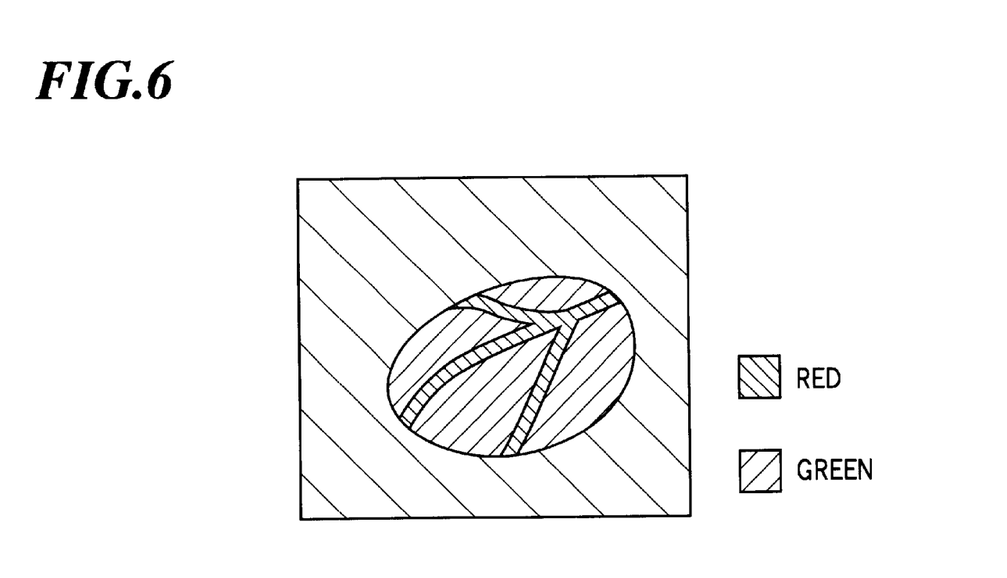
FIG. 6 illustrates an image in which the combined image data are separately colored and superimposed on the original image data for display.

For example, as seen in FIG. 6, portions indicated by positive value data contained in the combined image data $G(e_1, e_2)$, i.e., data on the contrast medium A may be displayed in red, and portions indicated by negative value data on the internal organ B may be displayed in green, further they may be superimposed on an image of the original image data $D(e_1)$ or $D(e_2)$. Effecting such processing would make the position of the internal organ, etc. apparent in a visual field and enable a pathologically changed tissue within the internal organ to be seen distinctly.

As set forth hereinabove, according to the present invention, there can be obtained image data containing the difference in the acoustic characteristics depending on the properties of each tissue, which could not be obtained by only the transmission/reception of ultrasonic waves at a single kind of transmission power. This enables tissues of internal organs, etc. different in not merely the shape but also in properties to be extracted for display on the screen. Consequently, in the ultrasonic diagnosis, the status of pathologically changed tissues can be diagnosed in addition to the finding of the pathologically changed tissues.

While illustrative and presently preferred embodiments of the present invention have been described in detail herein, it is to be understood that the inventive concepts may be otherwise variously embodied and employed and that the appended claims are intended to be construed to include such variations except insofar as limited by the prior art.

What is claimed is:

1. An ultrasonic imaging method comprising the steps of:
   (a) obtaining plural kinds of image data by transmitting plural kinds of ultrasonic waves at different transmission power and receiving the plural kinds of ultrasonic waves reflected from an object to be inspected; and
   (b) performing arithmetic by using the plural kinds of image data obtained at step (a) to thereby figure out new image data.

2. The ultrasonic imaging method according to claim 1, wherein:
   step (a) includes obtaining plural kinds of frame data by iterating a plurality of times a step of obtaining frame data by scanning ultrasonic waves at predetermined transmission power, while varying the transmission power of the ultrasonic waves to be transmitted, and
   step (b) includes performing arithmetic by using the plural kinds of frame data obtained at step (a) to figure out new frame data.

3. The ultrasonic imaging method according to claim 1, wherein:
   step (b) includes a step of combining two kinds of image data $D(e_1)$ and $D(e_2)$ obtained by transmitting and receiving ultrasonic waves respectively at transmission power $e_1$ and $e_2$, the step of combining including figuring out combined image data $G(e_1, e_2)$ from the following equation:

$$G(e_1, e_2) = k_2 \times D(e_2) - k_1 \times D(e_1)$$

where $k_1$ and $k_2$ are positive coefficients.

4. The ultrasonic imaging method according to claim 2, wherein:
   step (b) includes a step of combining two kinds of image data $D(e_1)$ and $D(e_2)$ obtained by transmitting and receiving ultrasonic waves respectively at transmission power $e_1$ and $e_2$, the step of combining including figuring out combined image data $G(e_1, e_2)$ from the following equation:

$$G(e_1, e_2) = k_2 \times D(e_2) - k_1 \times D(e_1)$$

where $k_1$ and $k_2$ are positive coefficients.

5. The ultrasonic imaging method according to claim 3, wherein the two kinds of image data are shortest interframe data.

6. The ultrasonic imaging method according to claim 4, wherein the two kinds of image data are shortest interframe data.

7. An ultrasonic imaging apparatus comprising:
   ultrasonic wave transmission/reception means having a plurality of ultrasonic transducers, for transmitting ultrasonic waves toward an object to be inspected and receiving the ultrasonic waves reflected from the object to output a detection signal;
   signal processing means for generating image data on the basis of the detection signal output from said ultrasonic wave transmission/reception means;
   control means for controlling said ultrasonic wave transmission/reception means to vary transmission power of the ultrasonic waves to be transmitted so as to transmit and receive plural kinds of ultrasonic waves at different transmission power;
   storage means for accumulating image data output from said signal processing means to thereby store plural kinds of image data obtained by transmitting and receiving plural kinds of ultrasonic waves at different transmission power; and
   arithmetic means for performing arithmetic by using the plural kinds of image data stored in said storage means to thereby figure out new image data.

8. The ultrasonic imaging apparatus according to claim 7, wherein:
   said storage means stores plural kinds of frame data obtained by scanning plural kinds of ultrasonic waves at different transmission power, and
   said arithmetic means performs arithmetic by using the plural kinds of frame data stored in said storage means to thereby figure out new frame data.

9. The ultrasonic imaging apparatus according to claim 8, wherein:
   said control means changes an address for designating a storage region in said storage means in accordance with transmission power of the ultrasonic waves to be transmitted.

10. The ultrasonic imaging apparatus according to claim 9, wherein:
    said plurality of ultrasonic transducers of said ultrasonic wave transmission/reception means are arranged one-dimensionally and receive echoes containing two-dimensional information on the object to be inspected.

11. The ultrasonic imaging apparatus according to claim 9, wherein:
    said plurality of ultrasonic transducers of said ultrasonic wave transmission/reception means are arranged two-dimensionally and receive echoes containing three-dimensional information on the object to be inspected.

12. The ultrasonic imaging apparatus according to claim 8, wherein:
    said plurality of ultrasonic transducers of said ultrasonic wave transmission/reception means are arranged one-dimensionally and receive echoes containing two-dimensional information on the object to be inspected.

13. The ultrasonic imaging apparatus according to claim 8, wherein:

said plurality of ultrasonic transducers of said ultrasonic wave transmission/reception means are arranged two-dimensionally and receive echoes containing three-dimensional information on the object to be inspected.

14. The ultrasonic imaging apparatus according to claim 7, wherein:

said control means changes an address for designating a storage region in said storage means in accordance with transmission power of the ultrasonic waves to be transmitted.

15. The ultrasonic imaging apparatus according to claim 14, wherein:

said plurality of ultrasonic transducers of said ultrasonic wave transmission/reception means are arranged one-dimensionally and receive echoes containing two-dimensional information on the object to be inspected.

16. The ultrasonic imaging apparatus according to claim 14, wherein:

said plurality of ultrasonic transducers of said ultrasonic wave transmission/reception means are arranged two-dimensionally and receive echoes containing three-dimensional information on the object to be inspected.

17. The ultrasonic imaging apparatus according to claim 7, wherein:

said plurality of ultrasonic transducers of said ultrasonic wave transmission/reception means are arranged one-dimensionally and receive echoes containing two-dimensional information on the object to be inspected.

18. The ultrasonic imaging apparatus according to claim 7, wherein:

said plurality of ultrasonic transducers of said ultrasonic wave transmission/reception means are arranged two-dimensionally and receive echoes containing three-dimensional information on the object to be inspected.

* * * * *

UNITED STATES PATENT AND TRADEMARK OFFICE
CERTIFICATE OF CORRECTION

PATENT NO. : 6,666,822 B2
DATED : December 23, 2003
INVENTOR(S) : Toshitaka Agano It is certified that error appears in the above-identified patent and that said Letters Patent is hereby corrected as shown below:

Column 7, lines 57-64 and Column 8, lines 1 and 2,
please change the claim in its entirety:
-- The ultrasonic imaging method according to claim 3, wherein:
    step (a) includes obtaining plural kinds of frame data by iterating a plurality of times a step of obtaining frame data by scanning the object by using ultrasonic waves at predetermined transmission power, while varying the transmission power of the ultrasonic waves to be transmitted, and
    step (b) includes combining two kinds of frame data $D(e_1)$ and $D(e_2)$ obtained by transmitting and receiving ultrasonic waves at transmission power $e_1$ and $e_2$ respectively to thereby obtain combined frame data $G(e_1, e_2)$ from the following equation:
$$G(e_1, e_2) = k_2 \times D(e_2) - k_1 \times D(e_1)$$
where $k_1$ and $k_2$ are positive coefficients. --

Column 8,
Lines 4 and 5, change "shortest interframe data" to -- included in nearest two frames, respectively --.
Line 7, change "image data are shortest interframe data" to -- frame data are included in nearest two frames, respectively --.
Line 28, change "performing arithmetic by using the plural kinds of image data stored in said storage means to thereby figure out new image data" to -- obtaining a new kind of image data on the. basis of the plural kinds of image data stored in said storage means to thereby extract am image of a specific portion from images represented by the plural kinds of image data --.
Line 34, after "scanning" insert -- the object by using the --.

UNITED STATES PATENT AND TRADEMARK OFFICE
CERTIFICATE OF CORRECTION

PATENT NO. : 6,666,822 B2
DATED : December 23, 2003
INVENTOR(S) : Toshitaka Agano It is certified that error appears in the above-identified patent and that said Letters Patent is hereby corrected as shown below:

Column 8, (cont.)
Lines 36-38, change "said arithmetic means performs arithmetic by using the plural kinds of frame data stored in said storage means to thereby figure out new frame data" to -- said arithmetic means obtaining a new kind of frame data on the basis of the plural kinds of frame data stored in said storage means to thereby extract an image of a specific portion from images represented by-the plural kinds. of frame data --.

Signed and Sealed this

Twentieth Day of July, 2004

JON W. DUDAS
*Acting Director of the United States Patent and Trademark Office*

UNITED STATES PATENT AND TRADEMARK OFFICE
CERTIFICATE OF CORRECTION

PATENT NO.     : 6,666,822 B2
DATED          : December 23, 2003
INVENTOR(S)    : Toshitaka Agano It is certified that error appears in the above-identified patent and that said Letters Patent is hereby corrected as shown below:

<u>Column 7,</u>
Lines 34-36, change "(b) performing arithmetic by using the plural kinds of image data obtained at step (a) to thereby figure out new image data" to -- (b) obtaining a new kind of image data on the basis of the plural kinds of image data obtained at step (a) to thereby extract an image of a specific portion from images represented by the plural kinds of image data --.
Line 41, after "scanning" insert -- the object by using --.
Lines 44 and 46, change "step (b) includes performing arithmetic by using the plural kinds of frame data obtained at step (a) to figure out new frame data" to -- step (b) includes obtaining a new kind of frame data on the basis of the plural kinds of frame data obtained at step (a) to thereby extract an image of a specific portion from images represented by the plural kinds of frame data --.
Lines 47 and 56, please change the claim in its entirety:
    -- An ultrasonic imaging method comprising the steps of:
    (a) obtaining plural kinds of image data by transmitting plural kinds of ultrasonic waves at different transmission power and receiving the plural kinds of ultrasonic waves reflected from an object to be inspected; and
    (b) combining two kinds of image data $D(e_i)$ and $D(e_2)$ obtained by transmitting and receiving ultrasonic waves at transmission power $e_1$ and $e_2$ respectively to thereby obtain combined image data $G(e_1, e_2)$ from the following equation:
$$G(e_1, e_2) = k_2 \times D(e_2) - k_1 \times D(e_1)$$
where $k_1$ and $k_2$ are positive coefficients. --

<u>Column 7, lines 57-64 and Column 8, lines 1 and 2,</u>
please change the claim in its entirety:
-- The ultrasonic imaging method according to claim 3, wherein:
    step (a) includes obtaining plural kinds of frame data by iterating a plurality of times a step of obtaining frame data by scanning the object by using ultrasonic waves at predetermined transmission power, while varying the transmission power of the ultrasonic waves to be transmitted, and
    step (b) includes combining two kinds of frame data $D(e_1)$ and $D(e_2)$ obtained by transmitting and receiving ultrasonic waves at transmission power $e_1$ and $e_2$ respectively to thereby obtain combined frame data $G(e_1, e_2)$ from the following equation:
$$G(e_1, e_2) = k_2 \times D(e_2) - k_1 \times D(e_1)$$
where $k_1$ and $k_2$ are positive coefficients. --

UNITED STATES PATENT AND TRADEMARK OFFICE
CERTIFICATE OF CORRECTION

PATENT NO.   : 6,666,822 B2
DATED        : December 23, 2003
INVENTOR(S)  : Toshitaka Agano It is certified that error appears in the above-identified patent and that said Letters Patent is hereby corrected as shown below:

<u>Column 8,</u>
Lines 4 and 5, change "shortest interframe data" to -- included in nearest two frames, respectively --.
Line 7, change "image data are shortest interframe data" to -- frame data are included in nearest two frames, respectively --.
Line 28, change "performing arithmetic by using the plural kinds of image data stored in said storage means to thereby figure out new image data" to -- obtaining a new kind of image data on the. basis of the plural kinds of image data stored in said storage means to thereby extract am image of a specific portion from images represented by the plural kinds of image data --.
Line 34, after "scanning" insert -- the object by using the --.
Lines 36-38, change "said arithmetic means performs arithmetic by using the plural kinds of frame data stored in said storage means to thereby figure out new frame data" to -- said arithmetic means obtaining a new kind of frame data on the basis of the plural kinds of frame data stored in said storage means to thereby extract an image of a specific portion from images represented by-the plural kinds. of frame data --.

This certificate supersedes Certificate of Correction issued July 20, 2004.

Signed and Sealed this

Thirtieth Day of November, 2004

JON W. DUDAS
*Director of the United States Patent and Trademark Office*